United States Patent [19]

Orkosalo

[11] Patent Number: 4,688,423
[45] Date of Patent: Aug. 25, 1987

[54] SYSTEM AND PROCESS FOR MEASURING ULTRASONIC VELOCITY

[75] Inventor: Jorma J. Orkosalo, San Jose, Calif.

[73] Assignee: Measurex Corporation, Cupertino, Calif.

[21] Appl. No.: 722,570

[22] Filed: Apr. 11, 1985

[51] Int. Cl.⁴ .............................................. G01N 29/04
[52] U.S. Cl. ...................................... 73/159; 73/598; 73/639; 310/334
[58] Field of Search .................. 73/597, 598, 635, 639, 73/159; 310/336, 334, 348, 369

[56] References Cited

U.S. PATENT DOCUMENTS

| | | | |
|---|---|---|---|
| 3,612,920 | 10/1971 | Bantz | 310/336 |
| 3,628,375 | 12/1971 | Pagano | 73/639 |
| 3,678,737 | 7/1972 | Miller | 310/336 |
| 3,822,588 | 7/1974 | Knight et al. | 73/81 |
| 4,291,577 | 9/1981 | Baum et al. | 73/597 |
| 4,302,976 | 12/1981 | Bull | 73/639 |
| 4,519,251 | 5/1985 | Dickson | 73/639 |
| 4,574,634 | 3/1986 | Pappano | 73/159 |

FOREIGN PATENT DOCUMENTS 1294404 10/1972 United Kingdom .
838402 6/1981 U.S.S.R. ................................. 73/159

OTHER PUBLICATIONS

"Development of a Sonic Modulus Test Device for the On-Line Measurement of Elastic Moduli of Wet Paper Webs" by Edwin J. Senko, a thesis submitted for the Master of Science Degree, State University of New York, College of Environmental Science and Forestry (Sep. 1983).
Lu Article in Jun. 1975 issue of Tappi Journal.

Primary Examiner—Howard A. Birmiel
Attorney, Agent, or Firm—Hal J. Bohner

[57] ABSTRACT

A system is provided for measuring the velocity of vibrations in a moving web, such as a sheet of paper. The system includes a transmitter coupled to the paper to transmit waves and a receiver to receive the waves. A signal processing system is used to determine the velocity.

18 Claims, 5 Drawing Figures

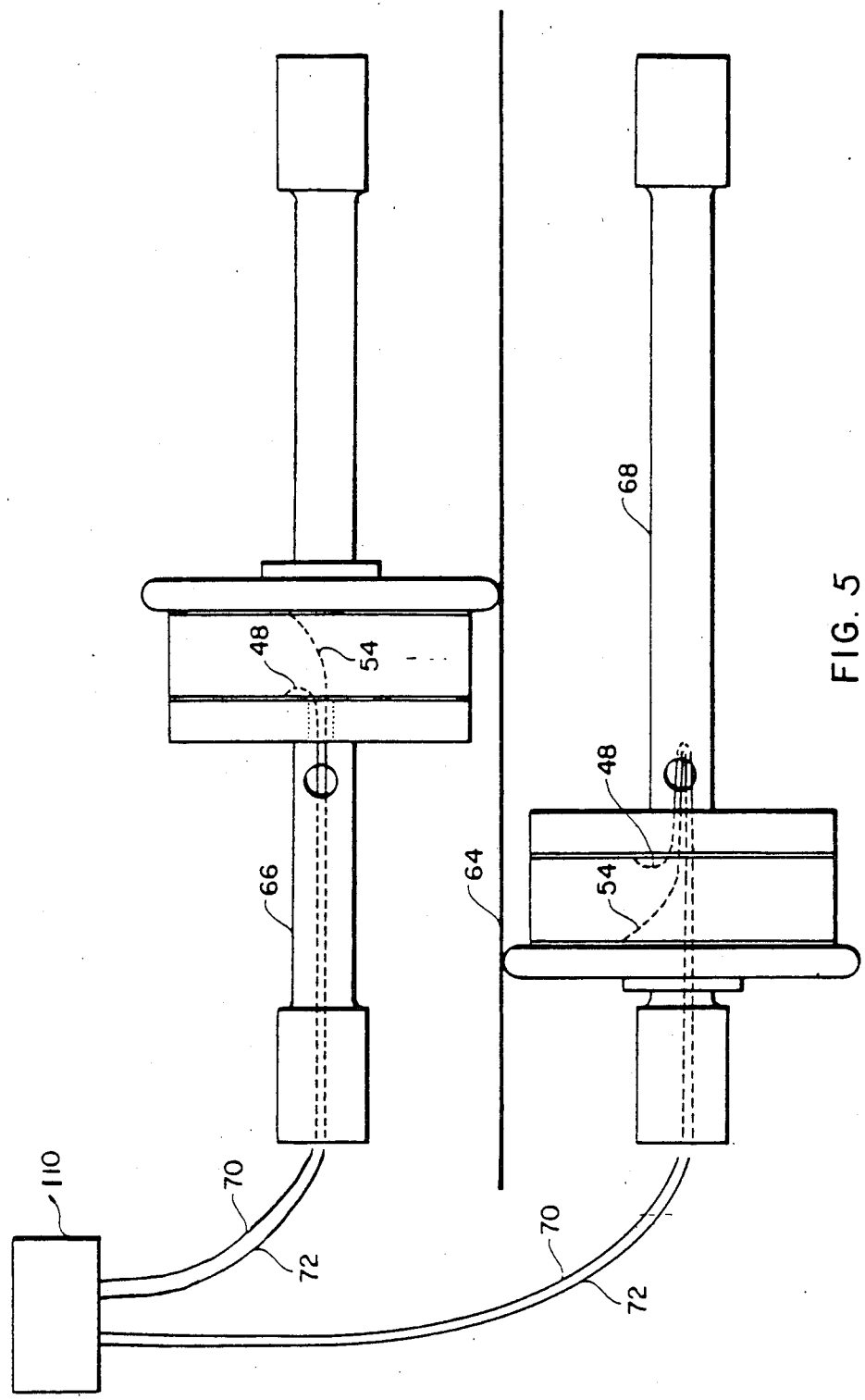

SYSTEM AND PROCESS FOR MEASURING ULTRASONIC VELOCITY

BACKGROUND OF THE INVENTION

1. The Field of The Invention

The present invention concerns a device for measuring the velocity of ultrasonic vibrations in a moving web such as a sheet of paper.

2. State of the Art

In the manufacture of paper it is often important to know the strength of the paper. Strength of paper can be tested in various ways including burst strength, tensile strength and pierce strength. Normally, these strength parameters are determined by various destructive tests in a laboratory. However, on-line determination of paper strength during the manufacture of the paper can aid in producing paper which can meet specified strength requirements.

U.S. Pat. No. 4,291,577, assigned to the Institute of Paper Chemistry, teaches a system for measuring the strength of paper as it is being produced. The patent provides for measurement of the velocity of ultrasound waves through the moving paper sheet. Based upon the velocity the strength of the paper can be determined.

The patent teaches a device having two wheels which are spaced apart from one another and which roll along the moving paper web. The first wheel contains a transducer in the form of a rectangular button mounted on the periphery of the wheel so that as the wheel rotates the button periodically contacts the paper. Each revolution of the wheel, when the transducer contacts the paper, it receives an electrical signal from a signal generator and imparts a mechnical signal to the paper. The second wheel contains a receiving transducer substantially the same as the transmitting transducer, which also is mounted on the periphery of the wheel and occupies a small percentage of the total circumference of the wheel. The receiving transducer contacts the paper once each revolution of the wheel and receives the signal from the transmitter by picking up the ultrasound signal from the paper and converting it to an electrical signal. The system also includes a position detector to monitor the rotational position of the first wheel and to trigger the firing of the ultrasound pulse by the transmitter when the wheel is in a predetermined position. The rotation of the receiving wheel is coordinated with the transmitting wheel so that the receiving transducer is in contact with the paper at the appropriate time to receive the transmitted signal. The signal from the receiving transducer is transmitted to a metering and recording apparatus which measures the velocity of the ultrasonic waves.

The system described in the patent has a number of disadvantages. Since the transmitting transducer and the receiving transducer each contact the paper during only a small percentage of the total rotation of the wheels, the rotation of the wheels must by carefully synchronized and the transmission of the pulse must be carefully timed so that the pulse is received by the transmitter when it is in contact with the paper. Furthermore, since the transmitter and the receiver are only in contact with the paper for a small percentage of the total rotation of the wheels, a substantial portion of the paper is not subject to velocity measurement.

OBJECTS OF THE INVENTION

An object of the present invention is to provide a system and process for continuously measuring the velocity of ultrasonic vibrations in a moving web. A further object is to provide such a system and process having transducers which can satisfactorily operate without being precisely synchronized with one another.

Futher objects and advantages of the present invention can be ascertained by reference to the specification and drawings herein which are offered by way of example and not in limitation of the invention which is defined by the claims and equivalents.

BRIEF DESCRIPTION OF THE DRAWINGS

FIG. 5 is an illustration of another alternative embodiment.

DETAILED DESCRIPTION OF THE PREFERRED EMBODIMENTS

Figure 1:
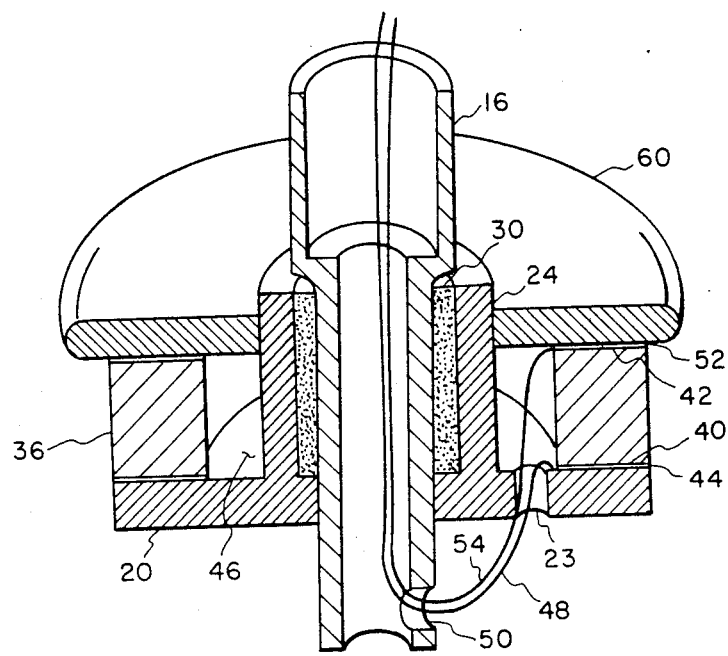
FIG. 1 is a cutaway view of one part of the present embodiment.

The present embodiment includes three transmitter-receiver members which are substantially the same as one another. FIG. 1 illustrates one of the transmitter-receivers. Each transmitter-receiver is mounted on an axle 16 which is hollow and substantially cylindrical. The axle 16 includes a central part whereon the transmitter-receivers are mounted, and end members which are coupled to bearings, not shown, for rotation. Each transmitter-receiver includes a support member which has a disc shaped part 20 having a central port. The disc shaped part 20 is coupled to a cylindrical part 24 which has a smaller outside diameter than the disc shaped part 20, and the cylindrical part 24 has a central port 26. A rubber bushing 30 is mounted inside the central port of the support member, and the bushing 30 is in turn mounted on the axle 16. Thus the support member is affixed to the axle to rotate therewith.

A piezoelectric transducer 36 is cylindrical and has two faces 40 and 42. The piezoelectric transducers 36 are formed of piezoelectric ceramic material which is compressed to form the desired shape of the transducer. The first face 40 of transducer 36 is coupled to a copper screen 44 which is substantially the same shape as the face 40. In turn the copper screen 44 is coupled to the disc shaped part 20 of the support member. The open interior of the transducer 36 has a substantially larger diameter than the outside diameter of the cylindrical part 24 of the support member. Thus a space 46 is formed between the interior of the piezoelectric transducer 36 and the cylindrical part 24. A wire 48 is coupled to the copper screen 44, and the wire extends through the space 46, and through a port 23 formed in the disc shaped part 20. The wire extends through a port 50 formed in the axle 16 and through the interior of the axle. The wire 48 then couples to a rotatable coupling, not shown, which permits the axle and wire 48 to rotate while transmitting an electrical signal to the coupling.

A second copper screen 52, substantially the same as the copper screen 44 is coupled to the face 42 of the piezoelectric transducer 36. A wire 54 is coupled to the copper screen 52, and the wire 54 follows substantially the same path as the wire 48. The copper screen 52 is connected to a wheel 60. The wheel 60 is disc shaped and has a central opening which is the same size as the outside diameter of the cylindrical part 24. The wheel 60 extends radially slightly beyond the piezoelectric transducer 36, and the outside of the wheel is smooth and rounded to permit it to contact the paper without damaging it.

Figure 2:
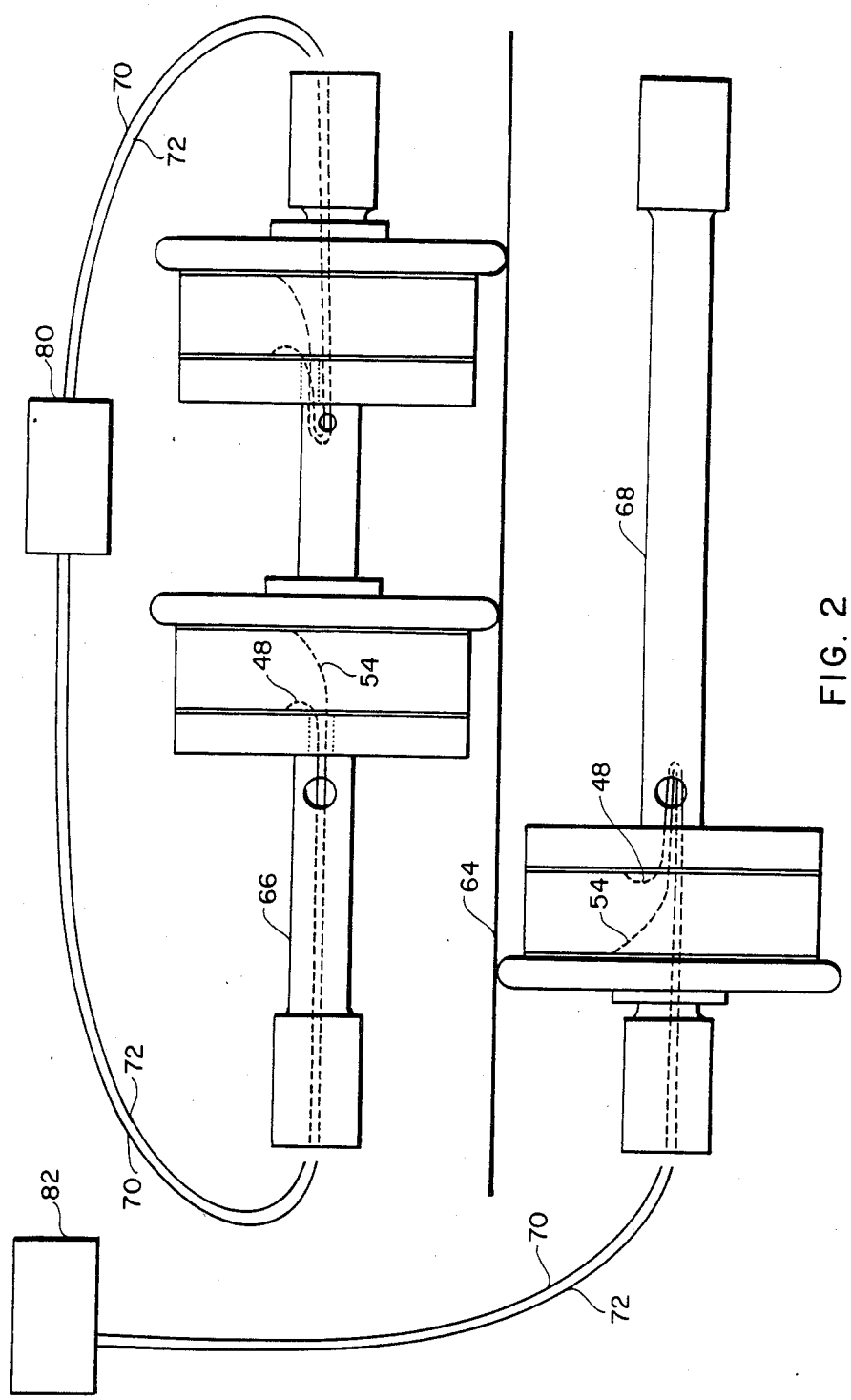
FIG. 2 is an illustration of one embodiment of the present invention.

Turning to FIG. 2 there are shown three transmitter-receivers mounted for operation in cooperation with a sheet of paper 64. Two transmitter-receivers are mounted on an upper axle 66, and one transmitter-receiver is mounted on a lower axle 68. The two upper transmitter-receivers are mounted with their wheels on the right side, and the lower transmitter-receiver 10 is mounted with its wheel on the left side. The upper and lower axles 66 and 68 are located so that the wheels 60 of each transmitter-receiver are in contact with the paper and the wheels rotate as the paper moves without sliding on the paper. The axles 66 and 68 rotate with the wheels 60.

The wires 48 and 54 from each transmitter-receiver 10 are coupled to rotatable couplings, not shown, which are mounted at the ends of the axles 66 and 68 and which permit electrical signals from the wires to be transmitted to stationary wires 70 and 72. The wires 70 and 72 from the upper axle 66 are connected to a signal processing and computing means 80 which receives the electrical signals from the wires and computes the velocity of the ultrasonic waves based on the information received. The wires 70 and 72 from the lower axle 68 are connected to a signal-generating means 82 which generates electric signals having a predetermined, controllable ultrasonic frequency.

In operation, two of the transmitter-receivers are designated as receivers and one is designated as a transmitter. In the embodiment shown in FIG. 2 the lower transmitter-receiver is designated as a transmitter and the upper two are designated as receivers. Thus a sine wave electrical signal having a predetermined frequency is transmitted by the signal generator 82 to the lower transmitter-receiver. The signals are received by the copper screens which in turn apply voltage bias across the piezoelectric transducer 36. This causes the transducer to expand and contract, the expansions and contractions having a amplitude and frequency corresponding to that of the electrical signal applied by signal generator 82. The mechanical vibration of the piezoelectric transducer 36 in turn causes the wheel 60 to vibrate thus imparting an ultrasonic vibration signal to the paper 64.

The ultrasonic vibration travels through the paper and imparts vibrations to the wheels 60 of the two transmitter-receivers coupled to the axle 66. The vibration of the wheels 60 in turn causes vibration of the piezoelectric transducers 36 in the two receivers, and the transducers 36 create electrical signals on the wires 70 and 72, the electrical signals having amplitude and frequency corresponding to the vibration of the wheels 60. The signal processor and computer 80 receives signals from the wires 70 and 72 and determines the phase difference, P, between the two transmitter-receivers. The computer 80 has been programmed with the precise, predetermined distance, D, between the two wheels 60, and thus the computer determines the velocity of the ultrasonic vibration in the paper 64 based upon the predetermined distance, D, and the phase difference, P, between the received ultrasonic waves.

Figure 3:
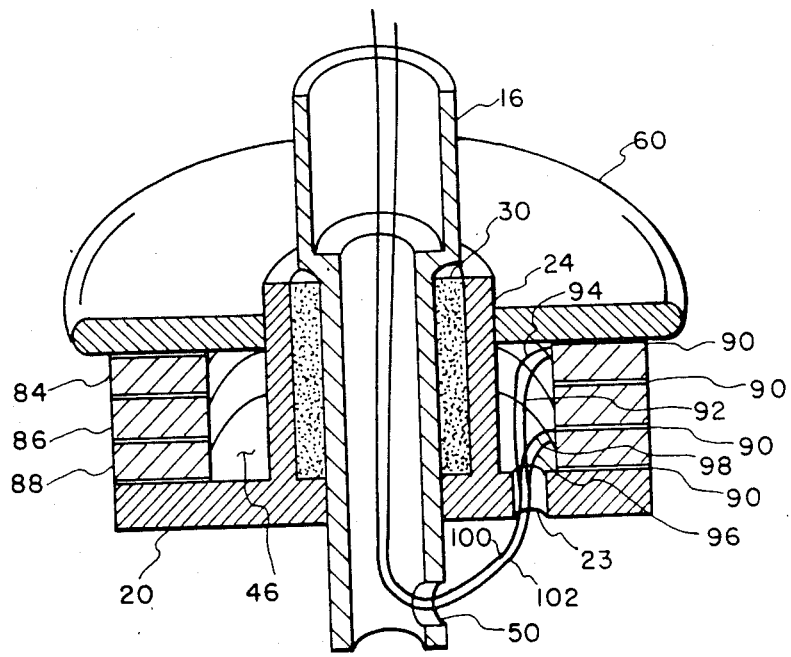
FIG. 3 is a cutaway view of one part of an alternative embodiment.

FIG. 3 shows an alternative embodiment in which three piezoelectric transducers 84, 86 and 88 are included in each transmitter-receiver. Each piezoelectric transducer 84, 86 and 88 is coupled to two copper screens 90 which are substantially the same as copper screens 52 and 54 discussed above. Wire 94 is coupled to the copper screen 90 nearest the wheel 60; wire 92 is coupld to the next lower copper screen; wire 98 is coupled to the next lower copper screen; and wire 96 is coupled to the copper screen which is between the lowest piezoelectric crystal 88 and the disc shaped part 20. Wires 92 and 96 are coupled to wire 100, and wires 94 and 98 are coupled to wire 102. Wires 100 and 102 pass through the ports 23 and 50. Apart from the piezoelectric crystals and related copper screens and wiring the transmitter-receiver in FIG. 3 is substantially the same as that in FIG. 1. When a transmitter-receiver is operated as a transmitter, electrical signals having the same amplitude, frequency, and phase are applied to each of the copper screens 90. Likewise when a transmitter-receiver is operated as a receiver, each of the copper screens receives electrical signals having substantially the same amplitude, phase and frequency.

Figure 4:
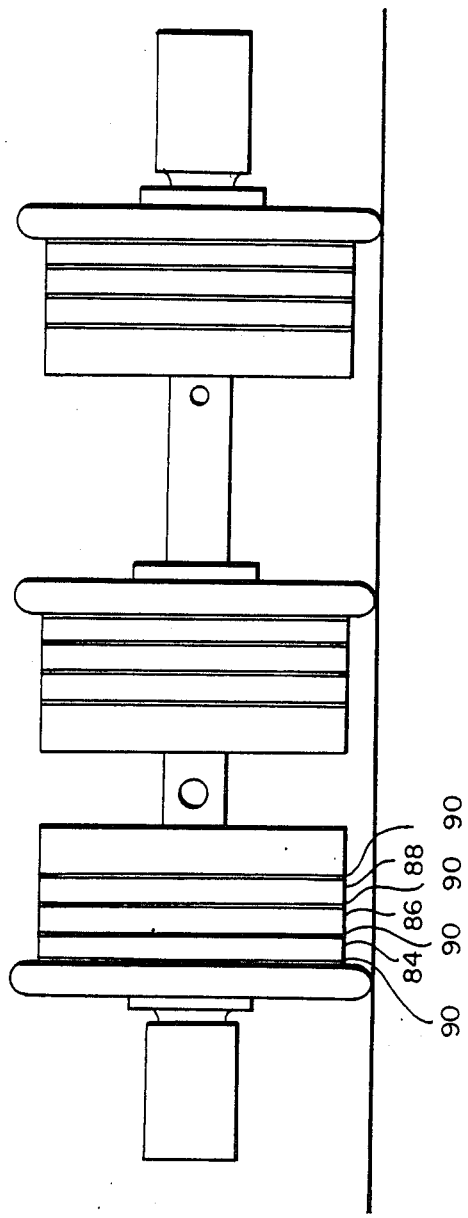
FIG. 4 is an illustration of an alternative embodiment of the present invention.

FIG. 4 illustrates an alternative embodiment of the present invention in which the transmitter and both receivers are mounted on the same axle.

In practice I have found that operation of the piezoelectric transducers in the range of 20,000 to 50,000 Hertz, and normally in the range of 20,000 to 25,000 Hertz is preferred. Frequencies above about 20 Kilo Hertz are normally considered ultrasonic. In some applications it may be desirable to operate my piezoelectric transducers below 20 Kilo Hertz, and such operation is within the scope of this invention. I have also found that it is important that the frequency of oscillation of the piezoelectric transducers 36 be carefully controlled relative to the mechnical characteristics of the wheel 60. The reason for this is that the vibrations of the piezoelectric transducers should set up standing waves in the wheels 60. Standing waves will be established only at certain frequencies which are dependent upon the size, shape and mechanical characteristics of the wheel 60. If a standing wave is not established then it is impossible to obtain usable information from the receivers. Furthermore, the standing waves in the wheels 60 should be such that the wheels are operating in a so-called "thickness mode" vibration and not a so-called "radial mode". In thickness mode type of vibration, the nodes of the standing waves are substantially circular and parallel to the periphery of the wheel 60. On the other hand, in the radial mode a plurality of nodes are formed at the periphery of the wheel. Thus if the wheel is operating with radial mode vibration, as the wheel rotates and contacts the paper, the amplitude of the signal imparted to the paper will be zero when a node is in contact with the paper, and will be a maximum when the point on a wheel, half-way between two nodes is in contact with the paper. Thus in this case the signal transmitted through the paper will oscillate between a maximum and zero thus making evaluation of the information received by the receivers very difficult if not impossible. On the other hand, if the wheel is vibrating in a thickness mode, the signal transmitted to the paper will not vary according to the rotational position of the wheel relative to the paper.

An alternative embodiment of the present system includes only two transducer-receivers, one operating in a transmission mode and one operating in receiving mode. This is illustrated in FIG. 5. This embodiment can be operated in two ways. In one mode of operation the distance between the transmitting wheel and the receiving wheel is carefully predetermined. Then a pulse of ultrasonic frequency is applied to the paper by the transmitting wheel and received by the receiving wheel. The time of travel of the pulse is determined and the velocity of the ultrasonic wave in the paper is determined based on the distance between the two wheels and the time of travel of the pulse. In another mode of operation signal generating and computing means 110 is coupled to both the transmitter coupled to axle 68 and the receiver coupled to axle 66. The signal generating and computing means 110 includes a phase locked amplifier which permits measurement of the phase difference between the continuously transmitted and continuously received signals. The distance between the two wheels is known and thus the velocity of the ultrasonic wave in the paper can be determined from the phase difference.

I have found that in some cases precautions should be taken to prevent signals from the transmitter from traveling through the air and reaching the receiver. If such precautions are not taken the transmitter can produce electromagnetic waves or sound waves which travel through the air and are received by the receiver, and the velocity of the waves through the air can be different from the velocity through the paper. Thus such waves through the air can create false readings of velocity. To prevent sound waves through the air from reaching the receiver, I have found that locating the transmitter and the receiver on opposite sides of the sheet is normally adequate. To prevent electromagnetic waves from the transmitter it is normally adequate to encase the transmitter and receiver, with the exception of the wheels which must contact the wheel, in Faraday cages and forming the wheels of a dielectric material such as glass, which does not generate electromagnetic waves.

I claim:

1. A system for measuring the velocity of vibrations in a moving web, comprising:
    (a) a transmitter which can be mounted in contact with the web to create vibrations in the web, the transmitter including a first wheel having an axis of rotation and which can be mounted with the periphery of the first wheel in contact with the web, the entire periphery of said first wheel being capable of transmitting vibrations, and a transducer mounted on the side of the first wheel symmetrically with respect to the axis of rotation;
    (b) a receiver which can be mounted in contact with the web to receive the vibrations generated by said transmitter and to convert these vibrations to an electrical signal;
    (c) signal processing means for receiving the electrical signal from the receiver and converting the signal to a measurement corresponding to the velocity of the vibrations in the web.

2. A system according to claim 1, wherein said transducer includes at least one piezoelectric disc coaxially mounted on the side of said first wheel for vibrating said first wheel at least throughout the entire periphery of said first wheel.

3. A system according to claim 1, wherein said receiver includes a second wheel which can rotate and which can be mounted in contact with the web, wherein at least the entire periphery of said second wheel is capable of receiving the vibrations which are converted to the electrical signal.

4. A system according to claim 5, wherein said receiver includes at least one piezoelectric disc mounted on the side of said second wheel for receiving the vibrations from at least the entire periphery of said second wheel.

5. A system according to claim 5, wherein said receiver further includes a third wheel which can rotate and which can be mounted in contact with the web at a position spaced apart from said second wheel, wherein at least the entire periphery of said third wheel is capable of receiving the vibrations which are converted to the electrical signal.

6. A process for measuring the velocity of vibrations in a moving web using a transmitter and a receiver which is capable of receiving vibrations from the web and converting the vibrations to electrical signals, the process comprising:
    (a) mounting the transmitter and the receiver in contact with the web spaced apart from one another a predetermined distance, D, the transmitter and receiver contacting opposite sides of the web;
    (b) generating a pulse with the transmitter;
    (c) receiving the pulse with the receiver;
    (d) determining the time, T, between generation of the pulse by the transmitter and reception of the pulse by the receiver; and
    (e) determining the velocity of the pulse based upon the time, T, and the predetermined distance, D.

7. A process for measuring the velocity of vibrations in a moving web using a transmitter which is capable of continuously transmitting vibrations to the web and also using two receivers which are capable of continuously receiving vibrations from the web, the process comprising:
    (a) mounting the transmitter and receivers in contact with the web with the transmitter spaced apart from both receivers and the receivers spaced apart from one another a predetermined distance, D, and wherein the transmitter contacts the side of the web opposite the side contacted by the receivers;
    (b) generating continuous vibrations in the web with the transmitter;
    (c) continuously receiving the vibrations with both receivers;
    (d) determining the phase difference, P, between the vibrations received by the two receivers;
    (e) determining the velocity of the vibrations based on the predetermined distance, D, and the phase difference, P.

8. A process for measuring the velocity of vibrations in a moving web using a transmitter which is capable of continuously transmitting vibrations to the web and a receiver which is capable of continuously receiving vibrations from the web, the process comprising:
    (a) mounting a transmitter and receiver in contact with the web with the transmitter spaced apart from the receiver by a predetermined distance, D, wherein the transmitter and receiver contact opposite sides of the web;
    (b) generating continuous vibrations in the web with the transmitter;
    (c) continuously receiving the vibrations with the receiver;

(d) computing the velocity of the vibrations in the moving web based on the phase difference between the vibrations at the transmitter and receiver.

9. A transmitter-receiver, comprising:
 (a) a rotatable wheel having an axis of rotation;
 (b) a first piezoelectric disk mounted coaxially on the side of said wheel; and
 (c) electrodes attached to the first piezoelectric disk to receive electrical signals produced by the first disk when the transmitter-receiver is used as a receiver and to transmit electrical signals to the first disk then the transmitter-receiver is used as a transmitter.

10. The transmitter-receiver of claim 9, further comprising at least one additional piezoelectric disk coaxially mounted on the side of the first disk opposite said wheel to produce electrical signals from received vibrations when the transmitter-receiver is used as a receiver and to convert electrical signals into vibrations then the transmitter-receiver is used as a transmitter.

11. The transmitter-receiver of claim 9, wherein the rotatable wheel is made of a dielectric material.

12. The transmitter-receiver of claim 9, wherein the periphery of the wheel is convex.

13. A system according to claim 3, wherein the peripheries of both the first wheel and the second wheel are convex.

14. A system according to claim 1, further comprising means for producing vibrations in the transducer at a frequency which induces thickness mode standing waves in the first wheel.

15. A system according to claim 1, further comprising means for causing the transducer to vibrate continuously during operation of the system.

16. The process of claim 6, wherein said transmitter and receiver rotatably contact the web.

17. The process of claim 7, wherein said transmitter and said receivers rotatably contact the web.

18. The process of claim 8, wherein said transmitter and receiver rotatably contact the web.

* * * * *

UNITED STATES PATENT AND TRADEMARK OFFICE
CERTIFICATE OF CORRECTION

PATENT NO. : 4,688,423
DATED : August 25, 1987
INVENTOR(S) : JORMA J. ORKOSALO

It is certified that error appears in the above-identified patent and that said Letters Patent is hereby corrected as shown below:

In the claims, in claim 4 at column 6, line 5, "5" should read --3--;

and in claim 5 at column 6 line 10, "5" should read --3--.

Signed and Sealed this

Fourteenth Day of March, 1989

*Attest:*

DONALD J. QUIGG

*Attesting Officer*  *Commissioner of Patents and Trademarks*